United States Patent
Garg et al.

(10) Patent No.: US 10,294,209 B2
(45) Date of Patent: May 21, 2019

(54) DIFUNCTIONAL MONOMER COMPOUNDS CONTAINING CLICKABLE PENDANT FURYL GROUP AND POLYMERS THEREFROM

(71) Applicant: COUNCIL OF SCIENTIFIC & INDUSTRIAL RESEARCH, New Delhi (IN)

(72) Inventors: Kavita Garg, Pune (IN); Deepshikha Chatterjee, Pune (IN); Prakash Purushottam Wadgaonkar, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 47 days.

(21) Appl. No.: 15/536,105

(22) PCT Filed: Dec. 16, 2015

(86) PCT No.: PCT/IN2015/050205
§ 371 (c)(1),
(2) Date: Jun. 14, 2017

(87) PCT Pub. No.: WO2016/098129
PCT Pub. Date: Jun. 23, 2016

(65) Prior Publication Data
US 2018/0016250 A1    Jan. 18, 2018

(30) Foreign Application Priority Data
Dec. 16, 2014 (IN) .......................... 3712/DEL/2014

(51) Int. Cl.
| | | |
|---|---|---|
| C08G 18/08 | (2006.01) | |
| C08G 18/00 | (2006.01) | |
| C08G 61/04 | (2006.01) | |
| C07D 307/42 | (2006.01) | |
| C08J 3/24 | (2006.01) | |
| C08G 18/77 | (2006.01) | |
| C08G 73/08 | (2006.01) | |
| C08G 69/32 | (2006.01) | |
| C08G 73/10 | (2006.01) | |
| C08G 18/24 | (2006.01) | |
| C08G 18/32 | (2006.01) | |
| C08G 18/48 | (2006.01) | |
| C08G 18/70 | (2006.01) | |
| C08G 63/66 | (2006.01) | |

(52) U.S. Cl.
CPC ......... *C07D 307/42* (2013.01); *C08G 18/242* (2013.01); *C08G 18/3206* (2013.01); *C08G 18/4833* (2013.01); *C08G 18/701* (2013.01); *C08G 18/771* (2013.01); *C08G 63/66* (2013.01); *C08G 69/32* (2013.01); *C08G 73/08* (2013.01); *C08G 73/1067* (2013.01); *C08J 3/24* (2013.01); *C08J 2375/04* (2013.01)

(58) Field of Classification Search
CPC .......................... C07D 307/42; C08G 18/701; C08G 18/3206; C08G 18/771; C08G 18/242; C08G 18/4833
USPC .............................. 528/58, 55, 48, 44; 520/1
See application file for complete search history.

(56) References Cited

FOREIGN PATENT DOCUMENTS

JP        61291566        * 12/1986

OTHER PUBLICATIONS

C. Gaina: "Thermally reversible cross-linked poly(ether-urethane)s", Express Polymer Letters, vol. 7, No. 7, May 2, 2013, pp. 636-650.
Qiao Tian et al: "A thermally remendable epoxy resin", Journal of Materials Chemistry, vol. 19, No. 9, Jan. 1, 2009, p. 1289.
PCT International Search Report (Form PCT/ISA/210), dated Mar. 11, 2016.
PCT Written Opinion of the International Searching Authority, dated Mar. 11, 2016.

* cited by examiner

*Primary Examiner* — Jessica Whiteley
(74) *Attorney, Agent, or Firm* — John P. White; Cooper & Dunham LLP

(57) ABSTRACT

The present invention discloses novel difunctional monomers compound containing pendant clickable furyl group of formula (I), process for the preparation and polymers prepared there from.

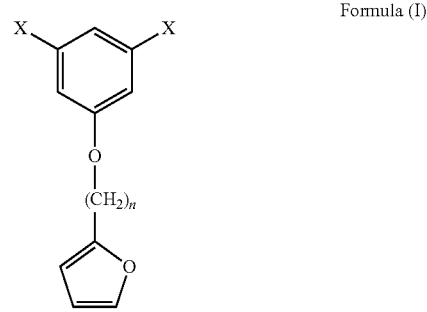

Formula (I)

wherein,
X is selected from —COOCH$_3$, —COOH, —CON$_3$, —NCO, —CONHNH$_2$, —CH$_2$OH n is selected from 2 to 12.

10 Claims, No Drawings

DIFUNCTIONAL MONOMER COMPOUNDS CONTAINING CLICKABLE PENDANT FURYL GROUP AND POLYMERS THEREFROM

CROSS-REFERENCE TO RELATED APPLICATIONS

This application is a § 371 national stage of PCT International Application No. PCT/IN2015/050205, filed Dec. 16, 2015, claiming priority of Indian Patent Application No. 3712/DEL/2014, filed Dec. 16, 2014, the content of each of which is hereby incorporated by reference into the application.

FIELD OF THE INVENTION

The present invention relates to novel difunctional monomers containing pendant clickable furyl group of formula (I) and process for the preparation of the same. Further, the present invention relates to polymers containing pendant clickable furyl group prepared from difunctional monomer compound of formula (I).

BACKGROUND AND PRIOR ART OF THE INVENTION

Polymers containing furyl functionality either at the chain end(s) or as pendant groups are of great interest in view of the demonstrated capability of the furyl moiety to participate in Diels-Alder reaction with suitable dienophiles which offers possibilities for their chemical modifications. Polymers possessing furyl groups at the chain ends have been synthesized either via chain polymerization by making use of furyl group-containing initiators, or by end group modification of prepolymers obtained via step growth polymerization with furyl containing reagents such as furfuryl amine or furfuryl alcohol. Polymers containing pendant furyl groups have been synthesized by the chain polymerization of addition monomers or by step growth polymerization of condensation monomers containing furyl groups. Chemical modification approach has also been employed to synthesize polymers with pendant furyl groups.

Polymers containing pendant furyl groups are of particular interest as they can undergo Diels-Alder reaction with suitable dienophiles such as bismaleimides resulting into the formation of crosslinked materials exhibiting thermoreversible characteristics and self-healing ability.

Article titled "Photosensitive poly(urethane acylsemicarbazide)s with azobenzene chromophores in the main chain" by A Palanisamy et al. published in *Journal of Applied Polymer Science*, 2004, 93 (1), pp 444-454 reports synthesis of poly(urethane acylsemicarbazide)s in a two-step process: (1) the in situ generation of diisocyanate through the thermal decomposition of an azobenzene-containing precursor diacyl azide and a reaction with ester/ether polyols to form an isocyanate-terminated prepolymer and (2) chain extension in N,N-dimethylacetamide with aliphatic or aromatic diacyl hydrazides.

Article titled "Diels-Alder-based crosslinked self-healing polyurethane/urea from polymeric methylene diphenyl diisocyanate" by P Du et al. published in *Journal of Applied Polymer Science*, 2014, 131 (9), pp 40234 reports synthesis of crosslinked self-healing polyurethane/urea based on a Diels-Alder reaction from a multiple-furan monomer and a commercial bismaleimide.

Article titled "Thermally reversible cross-linked poly(ether-urethane)s" by C Gaina et al published in *Express Polymer Letters*, 2013, 7 (7), pp 636-650 reports the synthesis of furan-containing poly(ether-urethane)s by the polyaddition reaction of 1,6-hexamethylene diisocyanate (HMDI) or 4,4'- dibenzyl diisocyanate (DBDI) to poly(tetramethylene ether) glycol and 2-[N,N-bis(2-methyl-2-hydroxyethyl)amino]furfuryl as chain extender by the solution prepolymer method.

Most of the reports pertaining to difunctional monomers containing pendant furyl group deal with aliphatic monomers. Thus, there is a need of aromatic difunctional monomers containing pendant furyl group which are useful for the preparation of polyurethanes, polyureas and high performance polymers viz., aromatic polyimides, aromatic polyamides, aromatic polyesters, aromatic polyhydrazides etc.

OBJECT OF INVENTION

The main objective of the present invention is to provide novel difunctional monomer compound of formula (I) containing clickable pendant furyl group.

Another objective of the present invention is to provide a process for the preparation of difunctional monomer compound of formula (I) containing clickable pendant furyl group.

Yet another objective of the present invention is to provide polymers prepared from difunctional monomer compound of formula (I) containing clickable pendant furyl group selected from but not limited to polyurethanes, polyureas and high performance polymers such as aromatic polyimides, aromatic polyamides, aromatic polyesters, aromatic polyhydrazides etc.

Still another objective of the present invention is to provide a process for the preparation of polyurethane from difunctional monomer compound of formula (I) containing clickable pendant furyl group.

Yet another objective of the present invention is to provide a polymer bearing difunctional monomers compound of formula (I) containing clickable pendant furyl group exhibiting thermo-reversible self-healing behavior.

SUMMARY OF THE INVENTION

Accordingly, the present invention provides novel difunctional monomer compound of formula (I) containing pendant clickable furyl group;

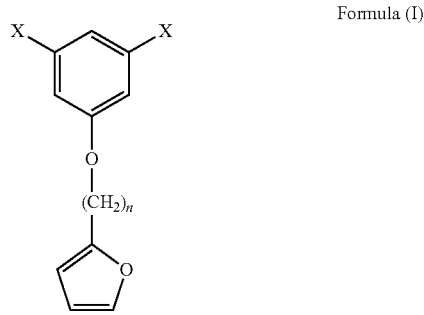

Formula (I)

Wherein;
X is selected from —COOCH$_3$, —COOH, —CON$_3$, —NCO, —CONHNH$_2$, —CH$_2$OH.
n is selected from 2 to 12.

In preferred embodiment, said difunctional monomer compound is selected from
  a) Dimethyl 5-((4-(furan-2-yl)butyl)oxy)isophthalate,
  b) Dimethyl 5-((6-(furan-2-yl)hexyl)oxy)isophthalate,
  c) 5-((4-(Furan-2-yl)butyl)oxy)isophthalic acid,
  d) 5-((6-(Furan-2-yl)hexyl)oxy)isophthalic acid,
  e) 5-((4-(Furan-2-yl)butyl)oxy)isophthaloyl azide,
  f) 5-((6-(Furan-2-yl)hexyl)oxy)isophthaloyl diazide,
  g) 2-(4-(3,5-Diisocyanatophenoxy)butyl)furan,
  h) 5-((4-(Furan-2-yl)butyl)oxy)isophthalohydrazide,
  i) 5-((6-(Furan-2-yl)hexyl)oxy)isophthalohydrazide,
  j) (5-((4-(Furan-2-yl)butyl)oxy)-1,3-phenylene)dimethanol,
  k) (5-((6-(Furan-2-yl)hexyl)oxy)-1,3-phenylene)dimethanol In one embodiment, the present invention provides a process for the preparation of novel difunctional monomer compound of formula (I) containing pendant clickable furyl group using 5-hydroxyisophthalic acid as a commercially available starting material, wherein said process comprising the steps of :
  a) Reacting 5-hydroxyisophthalic acid with methanol in presence of sulfuric acid followed by heating the reaction mixture at temperature in the range of 55 to 65° C. for the period of 8 to 10 h to afford dimethyl 5-hydroxyisophthalie;
  b) Etherification of the phenolic hydroxyl group of compound of step (a) using α-bromo-ω-furyl alkane to afford intermediate diester;
  c) Stirring the reaction mixture of intermediate diester of step (b) in ethanol and hydrazine hydradate at temperature in the range of 65 to 75° C. for the period of 9 to 12 h to afford 5-((furan-2-yl)alkyl)oxy)isophthalohydrazide;
  d) Subjecting intermediate diester of step (b) for reduction in presence of suitable reducing agent to afford (5-((furan-2-yl)alkyl)oxy-1,3-phenylene)dimethanol;
  e) Hydrolyzing the intermediate diester of step (b) to afford aromatic diacid monomers containing pendant furyl group connected via alkoxy chain;
  f) Reacting aromatic diacid monomers of step (e) with triethylamine and ethylchloroformate followed by reaction with sodium azide to afford 5-((furan-2-yl)alkyl)oxy)isophthaloyl azide;
  g) Heating the reaction mixture of diacyl azide of step (f) in toluene in presence of nitrogen atmosphere at temperature in the range of 70 to 90° C. for the period in the range of 3 to 8 h to afford 2-(3,5-diisocyanatophenoxy)alkyl)furan.

In preferred embodiment, said etherification is carried out at temperature in the range of 45 to 55° C. for the period of 6 to 9 h.

In another preferred embodiment, said alkaline hydrolysis is carried out by using suitable hydrolysis agent selected from sodium hydroxide or potassium hydroxide.

In still preferred embodiment, said alkaline hydrolysis is carried out at temperature in the range of 55 to 65° C. for the period in the range of 10 to 12 h.

In still preferred embodiment, said reducing agent in step (d) is selected from Lithium aluminium hydride (LiAlH$_4$) or combination of sodium borohydride and zinc chloride. In one embodiment, the present invention provides polymers prepared from difunctional monomer compound of formula (I) containing clickable pendant furyl group selected from but not limited to polyurethanes, polyureas and high performance polymers such as aromatic polyimides, aromatic polyamides, aromatic polyesters, aromatic polyhydrazides etc.

In another embodiment, the present invention provides a process for the preparation of polyurethane from new difunctional monomer compound containing pendant clickable furyl group of formula (I), wherein said process comprises heating the reaction mixture comprising of diacylazide monomer compound of formula (I) in toluene for 3 h at 70 to 90° C. followed by addition of dibutyltin dilaurate and diol dissolved in toluene and further heating the mixture for the period in the range of 7 to 9 h at the same temperature.

In preferred embodiment, said diacyl azide monomer compound of formula (I) is 5-((4-(furan-2-yl) butyl)oxy) isophthaloyl azide.

In another preferred embodiment, wherein diol is selected from α,ω-alkanediol, poly(ethylene glycol) and poly(tetramethylene glycol).

In another embodiment, the present invention provides a polymer bearing difunctional monomers compound of formula (I) containing clickable pendant furyl group exhibiting thermo-reversible self-healing behavior.

DETAILED DESCRIPTION OF THE INVENTION

The invention will now be described in detail in connection with certain preferred and optional embodiments, so that various aspects thereof may be more fully understood and appreciated.

In the view of above, the present invention provides difunctional monomer compound of formula (I) containing clickable pendant furyl group;

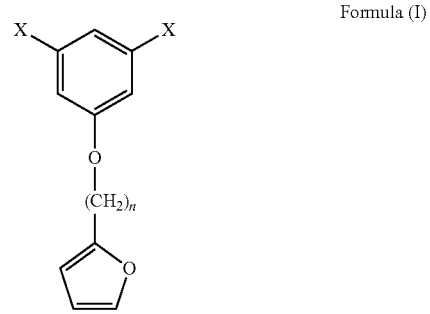

Formula (I)

Wherein,
X is selected from —COOCH$_3$, —COOH, —CON$_3$, —NCO, —CONHNH$_2$, —CH$_2$OH
n is selected from 2 to 12.

In preferred embodiment, said difunctional monomer compound is selected from
  a) Dimethyl 5-((4-(furan-2-yl)butyl)oxy)isophthalate,
  b) Dimethyl 5-((6-(furan-2-yl)hexyl)oxy)isophthalate,
  c) 5-((4-(Furan-2-yl)butyl)oxy)isophthalic acid,
  d) 5-((6-(Furan-2-yl)hexyl)oxy)isophthalic acid,
  e) 5-((4-(Furan-2-yl)butyl)oxy)isophthaloyl azide,
  f) 5-((6-(Furan-2-yl)hexyl)oxy)isophthaloyl diazide,
  g) 2-(4-(3,5-Diisocyanatophenoxy)butyl)furan,
  h) 5-((4-(Furan-2-yl)butyl)oxy)isophthalohydrazide,
  i) 5-((6-(Furan-2-yl)hexyl)oxy)isophthalohydrazide,
  j) (5-((4-(Furan-2-yl)butyl)oxy)-1,3-phenylene)dimethanol, k) (5-((6-(Furan-2-yl)hexyl)oxy)-1,3-phenylene)dimethanol The new difunctional monomers containing clickable pendant furyl group of general formula (I) may be diesters, diacids, diacyl azides, diisocyanates, diacyl hydrazides or diols.

In an embodiment, the present invention provides a process for the preparation of monomer compound of formula (I) using 5-hydroxyisopthalic acid as a commercially available starting material.

The process for the preparation of monomer compound of formula (I) comprising the steps of:
a) reacting 5-hydroxyisophthalic acid with methanol in presence of sulfuric acid followed by heating the reaction mixture at temperature in the range of 55 to 65° C. for the period of 8 to 10 h to afford dimethyl 5-hydroxyisophthalic;
b) etherification of the phenolic hydroxyl group of compound of step (a) using α-bromo-ω-furyl alkane to afford intermediate diester;
c) stirring the reaction mixture of intermediate diester of step (b) in ethanol and hydrazine hydradate at temperature in the range of 65 to 75° C. for the period of 9 to 12 h to afford 5-((furan-2-yl)alkyl)oxy)isophthalohydrazide;
d) subjecting intermediate diester of step (b) for reduction in presence of suitable reducing agent to afford (5-((furan-2-yl)alkyl)oxy-1,3-phenylene)dimethanol;
e) hydrolyzing the intermediate diester of step (b) to afford aromatic diacid monomers containing pendant furyl group connected via alkoxy chain;
f) reacting aromatic diacid monomers of step (e) with triethylamine and ethylchloroformate followed by reaction with sodium azide to afford 5-((furan-2-yl)alkyl)oxy)isophthaloyl azide;
g) heating the reaction mixture of diacyl azide of step (f) in toluene in presence of nitrogen atmosphere at temperature in the range of 70 to 90° C. for the period in the range of 3 to 8 h to afford 2-(3,5-diisocyanatophenoxy)alkyl)furan.

In preferred embodiment, said etherification is carried out at temperature in the range of 45 to 55° C. for the period of 6 to 9 h.

In another preferred embodiment, said alkaline hydrolysis in step (e) is carried out by using suitable hydrolysis agent selected from sodium hydroxide or potassium hydroxide.

In still preferred embodiment, said hydrolysis in step (e) is carried out at temperature in the range of 55 to 65° C. for the period in the range of 10 to 12 h.

In still preferred embodiment, said reducing agent in step (d) is selected from Lithium aluminium hydride (LiAlH$_4$) or combination of sodium borohydride and zinc chloride.

In preferred embodiment, the process for the preparation of difunctional monomer compound of formula (I) is as depicted in scheme 1.

Scheme: 1

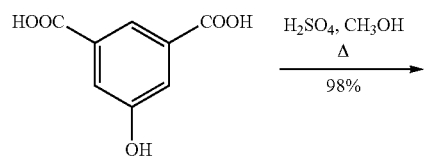

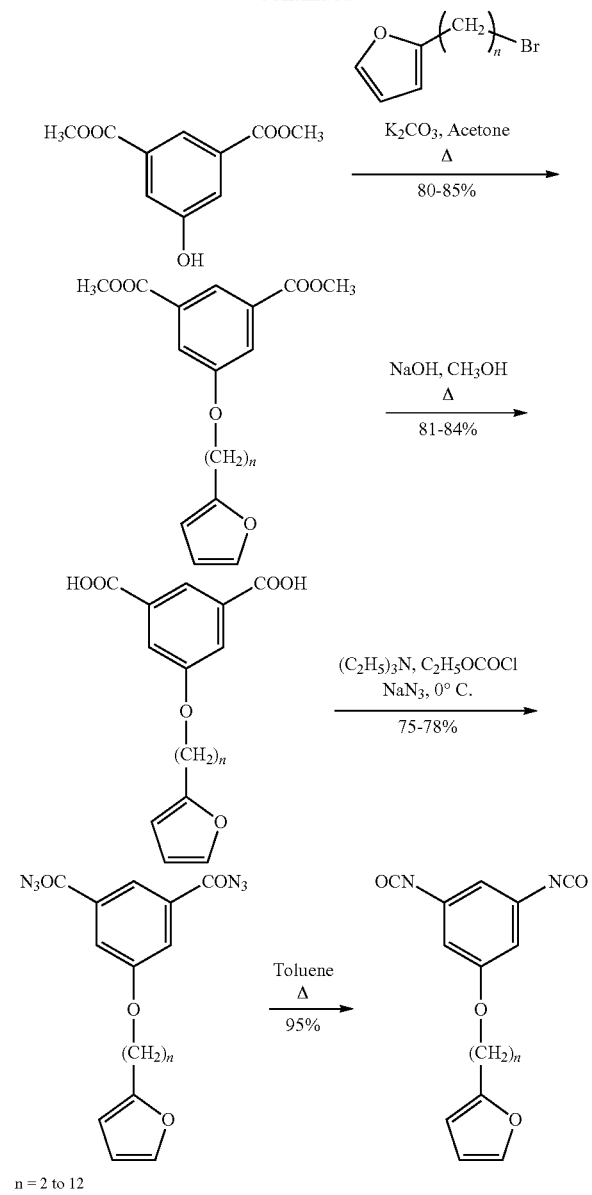

n = 2 to 12

In preferred another embodiment, the process for the synthesis of 5-((furan-2-yl)alkyl)oxy)isophthalohydrazide is as depicted in scheme 2.

Scheme: 2

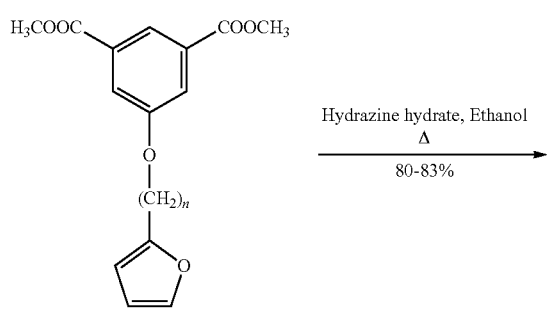

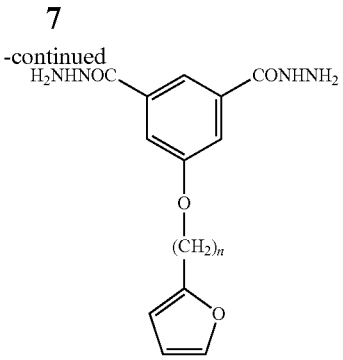

n = 2 to 12

In yet another embodiment, the process for the synthesis of (5-((furan-2-yl)alkyl)oxy-1,3-phenylene)dimethanol is as depicted in scheme 3.

Scheme: 3

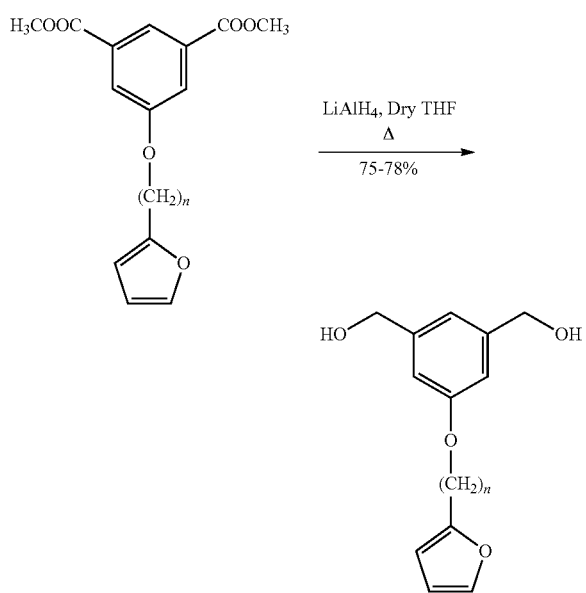

n = 2 to 12

In another embodiment, the monomers prepared by the process described herein are useful for the synthesis of polymers selected from, but not limited to polyurethanes, polyureas and high performance polymers such as aromatic polyimides, aromatic polyamides, aromatic polyesters, aromatic polyhydrazides etc. containing pendant furyl groups.

In a preferred embodiment, the polymers synthesized are self-healable/cross linkable polymers.

In one embodiment, the present invention is to provide a process for the preparation of polyurethane from difunctional monomer compound of formula (I) containing clickable pendant furyl group by polycondensation of 5-((4-(furan-2-yl)butyl)oxy)isophthaloyl azide with diol, wherein said process comprises heating the reaction mixture comprising of diacyl azide monomer of formula (I) in toluene for 3 h at 70 to 90° C. followed by the addition of catalyst and diol dissolved in toluene and further heating the mixture for the period in the range of 7 to 9 h at the same temperature.

In preferred embodiment, said catalyst is selected from dibutyltin dilaurate, Zirconium acetyl acetonate, 1,5,7-triazabicyclo[4.4.0]dec-5-ene, 1,8-biazabicyclo[5.4.0]undec-7-ene, 1,4-diazabicyclo[2.2.2]octane and triethylamine.

In another preferred embodiment, said diacyl azide monomer compound of formula (I) is 5-((4-(furan-2-yl)butyl)oxy) isophthaloyl azide.

In yet another preferred embodiment, wherein diol is selected from α,ω-alkanediol, poly(ethylene glycol) and poly(tetramethylene glycol).

The process for the synthesis of polyurethanes by polycondensation of 2-(4-(3,5-diisocyanatophenoxy)butyl)furan with diol is as depicted in scheme 4.

Scheme: 4

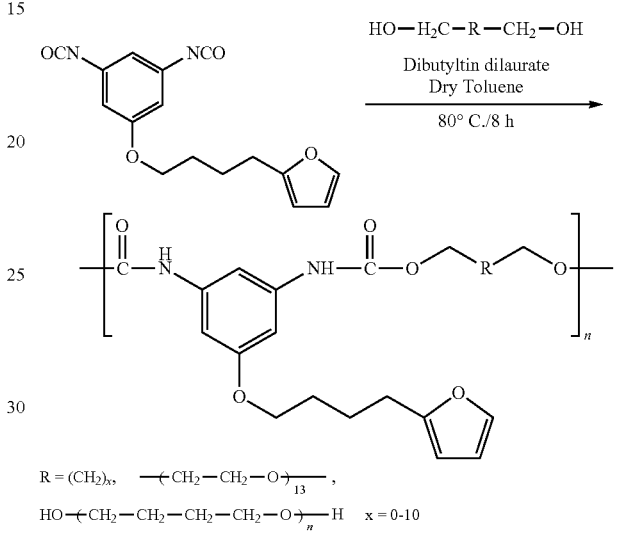

The following examples, which include preferred embodiments, will serve to illustrate the practice of this invention, it being understood that the particulars shown are by way of example and for purpose of illustrative discussion of preferred embodiments of the invention.

EXAMPLES

Following examples are given by way of illustration therefore should not be construed to limit the scope of the invention.

Example 1

Example 1a

Synthesis of dimethyl-5-hydroxyisophthalate

Into a 250 mL single-necked round bottom flask equipped with a magnetic stirring bar and a reflux condenser were placed 5-hydroxyisophthalic acid (25 g, $13.72 \times 10^{-2}$ mol), methanol (125 mL) and sulfuric acid (1 mL). The reaction mixture was heated at 65° C. for 10 h. The excess methanol was removed on a rotary evaporator. The residue was dissolved in chloroform (125 mL) and the solution was washed with water (2×70 mL). The organic layer was dried over anhydrous sodium sulfate, filtered and solvent was removed to obtain the crude product which was recrystallized from methanol to afford pure dimethyl-5-hydroxyisophthalate.

Yield: 98%; M.P. 162° C.; $^1$H NMR (400 MHz, CDCl$_3$): δ ppm=8.24 (s, 1H, Ar—H flanked by carbonyl), 7.77 (d, 2H, Ar—H, ortho to ether), 3.94 (s, 6H, —CH$_3$).

Example 1b

General Procedure for Synthesis of dimethyl 5-((furan-2-yl)alkyl)oxy)isophthalate Into a 100 mL three-necked round bottom flask equipped with a magnetic stirring bar, a reflux condenser and an addition funnel were placed dimethyl-5-hydroxy isophthalate (6 g, 28.5×10$^{-3}$ mol), potassium carbonate (5.9 g, 42.8×10$^{-3}$ mol) and acetone (80 mL). The solution of 2-(4-bromobutyl)furan or 2-(6-bromohexyl)furan (28.5×10$^{-3}$ mol) in acetone (10 mL) was added over a period of 30 min and the reaction mixture was stirred at the temperature of 55° C. for 8 h. The reaction mixture was filtered while hot. The filtrate was cooled and isolated crystals were dried at 40° C. under vacuum. The crude product was purified by column chromatography using pet ether:ethyl acetate (90:10, v/v) as an eluent to afford pure dimethyl 5-((furan-2-yl) alkyl)oxy)isophthalate.

1. Dimethyl 5-((4-(furan-2-yl)butyl)oxy)isophthalate:
   Yield: 80%; M.P.=74° C.; $^1$H NMR (400 MHz, CDCl$_3$): δ ppm=8.28 (s, 1 H, Ar—H flanked by carbonyl), 7.75 (d, 2H, Ar—H, ortho to ether), 7.32 (s, 1H, C$_5$-furyl), 6.3 (d, 1H, C$_4$-furyl), 6.04 (d, 1H, C$_3$-furyl), 4.07 (t, 2H, —CH$_2$), 3.95 (s, 6H, —CH$_3$), 2.73 (t, 2H, —CH$_2$), 1.85-1.90 (m, 4H, —CH$_2$—CH$_2$).

2. Dimethyl 5-((6-(furan-2-yl)hexyl)oxy)isophthalate
   Yield: 85%; M.P.=68° C.; $^1$H NMR (400 MHz, CDCl$_3$): δ ppm=8.27 (s, 1 H, Ar—H flanked by carbonyl), 7.74 (d, 2H, Ar—H, ortho to ether), 7.30 (s, 1H, C$_5$-furyl), 6.28 (d, 1H, C$_4$-furyl), 5.99 (d, 1H, C$_3$-furyl), 4.04 (t, 2H, —CH$_2$), 3.94 (s, 6H, —CH$_3$), 2.65 (t, 2H, —CH$_2$), 1.79-1.85 (m, 2H, —CH$_2$), 1.65-1.70 (m, 2H, —CH$_2$), 1.40-1.54 (mm, 4H, —CH$_2$—CH$_2$).

Example 1c

General Procedure for Synthesis of 5-((furan-2-yl)alkyl)oxy)isophthalic acid

Into a 250 mL single-necked round bottom flask equipped with a magnetic stirring bar and a reflux condenser were charged sodium hydroxide (1.20 g, 30.0×10$^{-3}$ mol), water (25 mL), methanol (25 mL) and dimethyl 5-((4-(furan-2-yl) butyl)oxy)isophthalate or dimethyl 5-((6-(furan-2-yl)hexyl) oxy)isophthalate (12×10$^{-3}$ mol) and the reaction mixture was heated at 65° C. for the period of 10 h. The reaction mixture was cooled to room temperature and acidified with dil HCl. The product was isolated by filtration and washed with water, and dried at 80° C. under vacuum overnight. The crude product was recrystallized from ethanol and water mixture to afford pure 5-((furan-2-yl)alkyl)oxy)isophthalic acid.

1. 5-((4-(Furan-2-yl)butyl)oxy)isophthalic acid:
   Yield: 84%; $^1$H-NMR (400 MHz, DMSO-d$_6$): δ ppm=13.27 (s, —OH), 8.06 (s, 1H, Ar—H flanked by carbonyl), 7.63 (d, 2H, Ar—H, ortho to ether), 7.49 (s, 1H, C$_5$-furyl), 6.33 (d, 1H, C$_4$-furyl), 6.11 (d, 1H, C$_3$-furyl), 4.09 (t, 2H, —CH$_2$), 2.67 (t, 2H, —CH$_2$), 1.7-1.78 (m, 4H, —CH$_2$—CH$_2$). $^{13}$C-NMR (100 MHz, DMSO-d$_6$): δ ppm=166.6, 158.9, 155.6, 141.4, 132.8, 122.3, 119.2, 110.5, 105.3, 67.9, 28.2, 27.1, 24.3.

2. 5-((6-(Furan-2-yl)hexyl)oxy)isophthalic acid:
   Yield: 81%; $^1$H-NMR (500 MHz, DMSO-d$_6$): δ ppm=13.31 (s, —OH), 8.06 (s, 1H, Ar—H flanked by carbonyl), 7.62 (d, 2H, Ar—H, ortho to ether), 7.47 (s, 1H, C$_5$-furyl), 6.32 (t, 1H, C$_4$-furyl), 6.06 (d, 1H, C$_3$-furyl), 4.05 (t, 2H, —CH$_2$), 2.59 (t, 2H, —CH$_2$), 1.69-1.75 (m, 2H, —CH$_2$), 1.56-1.62 (m, 2H, —CH$_2$), 1.37-1.47 (mm, 4H, —CH$_2$—CH$_2$). $^{13}$C-NMR (126 MHz, DMSO-d$_6$): δ ppm=166.9, 159.2, 156.1, 141.5, 133.0, 122.6, 119.4, 110.7, 105.4, 68.5, 28.9, 28.7, 28.0, 27.6, 25.6.

Example 1d

General Procedure for Synthesis of 5-((furan-2-yl)alkyl)oxy)isophthaloyl azide

Into a 100 mL two-necked round bottom flask equipped with an addition funnel, a thermowell and a magnetic stirring bar were placed 5-((4-(furan-2-yl)butyl)oxy-isophthalic acid or 5-((6-(furan-2-yl)hexyl)oxy)isophthalic acid (6.0×10$^{-3}$ mol) and acetone (7 mL). The reaction mixture was cooled to 0° C. and the solution of triethylamine (3.16 g, 31×10$^{-3}$ mol) in acetone (6 mL) was added dropwise over a period of 15 min. To the clear solution formed was added ethylchloroformate (3.39 g, 31×10$^{-3}$ mol) dropwise over a period of 10 min and stirred for 4 h. The solution of activated sodium azide (3.9 g, 60×10$^{-3}$ mol) in water (10 mL) was added dropwise over a period of 15 min and the reaction mixture was stirred at 0° C. for 4 h. Cold water (100 mL) was added gradually to the reaction mixture when the product precipitated out. The precipitate was separated by filtration and washed with cold water (100 mL). The product was dissolved in dichloromethane (25 mL), and the solution was dried over anhydrous sodium sulphate, filtered and dichloromethane was removed under reduced pressure at room temperature 35° C. to afford 5-((furan-2-yl)alkyl)oxy) isophthaloyl azide.

1. 5-((4-(Furan-2-yl)butyl)oxy)isophthaloyl azide
   Yield: 75%; $^1$H NMR (400 MHz, CDCl$_3$): δ ppm=8.22 (s, 1H, Ar—H flanked by carbonyl), 7.75 (d, 2H, Ar—H, ortho to ether), 7.31 (s, 1H, C$_5$-furyl), 6.29 (d, 1H, C$_4$-furyl), 6.02 (d, 1H, C$_3$-furyl), 4.05 (t, 2H, —CH$_2$), 2.72 (t, 2H, —CH$_2$), 1.83-1.89 (m, 4H, —CH$_2$—CH$_2$).

2. 5-((6-(Furan-2-yl)hexyl)oxy)isophthaloyl diazide
   Yield: 78%; $^1$H NMR (400 MHz, CDCl$_3$): δ ppm=8.22 (s, 1H, Ar—H flanked by carbonyl), 7.77 (d, 2H, Ar—H, ortho to ether), 7.31 (s, 1H, C$_5$-furyl), 6.28 (d, 1H, C$_4$-furyl), 5.99 (d, 1H, C$_3$-furyl), 4.04 (t, 2H, —CH$_2$), 2.65 (t, 2H, —CH$_2$), 1.80-1.85 (m, 2H, —CH$_2$), 1.68-1.71 (m, 2H, —CH$_2$), 1.49-1.53 (m, 4H, —CH$_2$—CH$_2$).

Example 1e

General Procedure for Synthesis of 2-(3,5-diisocyanatophenoxy)alkyl)furan

Into a 100 mL three-necked round bottom flask equipped with a magnetic stirring bar, a nitrogen inlet tube and a reflux condenser were placed 5-((4-(furan-2-yl)butyl)oxy) isophthaloyl azide (3.7×10$^{-3}$ mol) and dry toluene (20 mL). Nitrogen gas was bubbled gently through the reaction mixture. The reaction mixture was heated at ~85° C. for 5 h. Evaporation of toluene under reduced pressure afforded 2-(3,5-diisocyanatophenoxy)alkyl)furan.

1. 2-(4-(3,5-Diisocyanatobutyl)furan
   Yield: 95%; $^1$H NMR (400 MHz, CDCl$_3$): δ ppm=7.32 (s, 1H, C$_5$-furyl), 6.47 (d, 2H, Ar—H, ortho to ether), 6.43 (s, 1H, Ar—H flanked by isocyanato), 6.30 (d, 1H, C$_4$-furyl), 6.03 (s, 1H, C$_3$-furyl), 3.93 (d, 2H, —CH$_2$), 2.72 (s, 2H, —CH$_2$), 1.8-1.85 (m, 4H, —CH$_2$—CH$_2$); $^{13}$C NMR (100 MHz, CDCl$_3$): δ ppm=160.5, 155.6, 140.9, 135.2, 125.2, 113.5, 110.1, 108.9, 105.1, 68.1, 28.4, 27.6, 24.5.

Example 1f

General Synthesis of 5-((furan-2-yl)alkyl)oxy)isophthalohydrazide

Into a 50 mL two-necked round bottom flask equipped with an addition funnel and a reflux condenser fitted with a guard tube were placed dimethyl 5-((4-(furan-2-yl)butyl)oxy)isophthalate or dimethyl 5-((6-(furan-2-yl)hexyl)oxy)isophthalate (6×10$^{-3}$ mol) and ethanol (20 mL). Hydrazine hydradate 99% (1 g, 31×10$^{-3}$ mol) was added dropwise over a period of 15 min. The reaction mixture was stirred at 75° C. for 10 h. Cold water (50 mL) was added gradually to the reaction mixture when the product precipitated out. The precipitate was separated by filtration and washed with cold water (50 mL). The crude product was recrystallized from ethanol and tetrahydrofuran mixture to afford pure 5-((furan-2-yl)alkyl)oxy)isophthalohydrazide.

1. 5-((4-(Furan-2-yl)butyl)oxy)isophthalohydrazide

Yield: 83%; M.P.=162° C.; $^1$H NMR (400 MHz, DMSO-d$_6$): δ ppm=9.79 (s, 2H, —NH), 7.85 (s, 1H, Ar—H flanked by carbonyl), 7.50 (s, 1H, C$_5$-furyl), 7.46 (s, 2H, Ar—H, ortho to ether), 6.34 (t, 1H, C$_4$-furyl), 6.11 (d, 2H, C$_3$-furyl), 4.51 (s, 4H, —NH$_2$), 4.07 (t, 2H, —CH$_2$), 2.68 (s, 2H, —CH$_2$), 1.74-1.79 (m, 4H, —CH$_2$—CH$_2$).

2. 5-((6-(Furan-2-yl)hexyl)oxy)isophthalohydrazide

Yield: 80% ; M.P.=159° C.; $^1$H NMR (500 MHz, DMSO-d$_6$): δ ppm=9.81 (s, 2H, —NH), 7.85 (s, 1H, Ar—H flanked by carbonyl), 7.48 (s, 1H, C$_5$-furyl), 7.46 (s, 2H, Ar—H, ortho to ether), 6.33 (s, 1H, C$_4$-furyl), 6.07 (d, 2H, C$_3$-furyl), 4.54 (s, 4H, —NH$_2$), 4.03 (t, 2H, —CH$_2$), 2.6 (t, 2H, —CH$_2$), 1.70-1.75 (m, 2H, —CH$_2$), 1.57-1.63 (m, 2H, —CH$_2$), 1.36-1.47 (mm, 4H, —CH$_2$—CH$_2$); $^{13}$C NMR (126 MHz, CDCl$_3$): δ ppm=165.6, 158.9, 156.1, 141.6, 135.2, 118.8, 115.7, 110.7, 105.4, 68.3, 28.9, 28.7, 28.0, 27.6, 25.6.

Example 1g:

General Procedure for Synthesis of (5-((furan-2-yl)alkyl)oxy-1,3-phenylene)dimethanol Into a 100 mL three-necked round bottom flask equipped with an addition funnel, a reflux condenser and a nitrogen inlet were placed lithium aluminium hydride (0.68 g, 18×10$^{-3}$ mol) and dry tetrahydrofuran (40 mL). The reaction mixture was cooled to 0° C. and the solution of dimethyl 5-((4-(furan-2-yl)butyl)oxy)isophthalate or dimethyl 5-((6-(furan-2-yl)hexyl)oxy)isophthalate (6×10$^{-3}$ mol) in dry tetrahydrofuran (15 mL) was added dropwise over a period of 15 min under nitrogen atmosphere. After completion of addition, the reaction mixture was heated at 60° C. for 10 h. The reaction mixture was cooled to 0° C. and dil HCl was added to quench excess lithium aluminium hydride and the solution was filtered. The filtrate was diluted with tetrahydrofuran (20 mL) and solution was washed with brine water (2×50 mL). The organic layer was dried over anhydrous sodium sulfate, filtered and solvent was removed to obtain the crude product which was recrystallized from ethanol and water mixture to afford pure (5-((furan-2-yl)alkyl)oxy)-1,3-phenylene)dimethanol.

1. (5-((4-(Furan-2-yl)butyl)oxy)-1,3-phenylene)dimethanol

Yield: 78%; M.P.=73° C.; $^1$H NMR (400 MHz, CDCl$_3$): δ ppm=7.31 (s, 1H, C$_5$-furyl), 6.88 (s, 1H, Ar—H), 6.79 (s, 2H, Ar—H, ortho to ether), 6.29 (t, 1H, C$_4$-furyl), 6.01 (d, 2H, C$_3$-furyl), 4.59 (s, 4H, —CH$_2$—OH), 3.96 (t, 2H, —CH$_2$), 2.70 (s, 2H, —CH$_2$), 2.53 (s, 2H, —OH), 1.79-1.83 (m, 4H, —CH$_2$—CH$_2$). $^{13}$C NMR (100 MHz, CDCl$_3$): δ ppm=159.4, 155.9, 142.8, 140.8, 117.4, 112.1, 110.1, 104.9, 67.6, 65.0, 28.7, 27.6, 24.6.

2. (5-((6-(Furan-2-yl)hexyl)oxy)-1,3-phenylene)dimethanol

Yield: 75%; $^1$H NMR (500 MHz, CDCl$_3$): δ ppm=7.31 (s, 1H, C$_5$-furyl), 6.92 (s, 2H, Ar—H, ortho to ether), 6.83 (s, 1H, Ar—H), 6.29 (t, 1H, C$_4$-furyl), 5.99 (d, 2H, C$_3$-furyl), 4.65 (s, 4H, —CH$_2$—OH), 3.97 (t, 2H, —CH$_2$), 2.64 (t, 2H, —CH$_2$), 1.76-1.82 (m, 2H, —CH$_2$), 1.65-1.71 (m, 2H, —CH$_2$), 1.40-1.51 (mm, 4H, —CH$_2$—CH$_2$).

Example 2

Synthesis of Polyurethanes by Polycondensation of 2-(4-(3,5-diisocyanatophenoxy)butyl)furan with diol Into a 100 mL two-necked round bottom flask equipped with a reflux condenser and argon inlet were charged, 5-((4-(Furan-2-yl)butyl)oxy)isophthaloyl azide (0.5 g, 1.6×10$^{-3}$ mol) in dry toluene (20 mL). The reaction mixture was heated at 80° C. for 3 h to generate in situ 2-(4-(3,5-diisocyanatophenoxy)butyl)furan. To the reaction mixture was added dibutyltin dilaurate (1×10$^{-4}$ mol) and dacanediol or polyethylene glycol Mn=600 (1.4×10$^{-3}$ mol) dissolved in dry toluene (2 mL) with vigorous stirring. The reaction mixture was heated at 80° C. for 8 h. The toluene was removed under reduced pressure to afford solid polymer. The polymer was dissolved in tetrahydrofuran and the solution was poured into excess methanol. The precipitated polymer was filtered and dried under reduced pressure at 50° C. for 24 h.

Yield: 93%; FT-IR (KBr, cm$^{-1}$)—3430 (—NH), 1699 (C=O); $^1$H-NMR (CDCl$_3$, δ/ppm): 7.20 (s, 1H, C$_5$-furyl), 6.95 (s, —NH), 6.95 (s, 1H, C$_4$-furyl), 6.71 (s, 2H, Ar—H, ortho to ether), 6.18 (s, 1H, Ar—H flanked by urethane), 5.90 (s, 1H, C$_3$-furyl), 4.04 (t, 2H, —CH$_2$—O), 3.83 (t, 2H, —CH$_2$), 2.57 (t, 2H, —CH$_2$), 1.68-1.54 (m, 8H), 1.20 (br. s, 10H, —CH$_2$—CH$_2$—O).

ADVANTAGES OF THE PRESENT INVENTION

Versatile difunctional monomers containing clickable pendant furyl group.

The process uses simple, easily available and cheap starting material.

The monomers are suitable for the preparation of a host of polymers.

The invention claimed is:

1. A difunctional monomer compound containing clickable pendant furyl group of general formula (I);

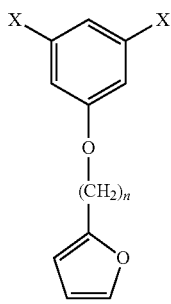

Formula (I)

wherein,
X is selected from —COOCH$_3$,—COOH, —CON$_3$, —NCO, —CONHNH$_2$, —CH$_2$OH n is selected from 2 to 12.

2. The compound as claimed in claim 1, wherein said difunctional monomer compound of formula (I) is selected from
   a) Dimethyl 5-((4-(furan-2-yl)butyl)oxy)isophthalate,
   b) Dimethyl 5-((6-(furan-2- yl)hexyl)oxy)isophthalate,
   c) 5-((4-(Furan-2-yl)butyl)oxy)isophthalic acid,
   d) 5-((6-(Furan-2- yi)hexyl)oxy)isophthalic acid,
   e) 5-((4-(Furan-2-yl)butyl)oxy)isophthaloyl azide,
   f) 5-((6-(Furan-2-yl)hexyl)oxy)isophthaloyl diazide,
   g) 2-(4-(3,5-Diisocyanatophenoxy)butyl)furan,
   h) 5-((4-(Furan-2-yl)butyl)oxy)isophthalohydrazide,
   i) 5-((6-(Furan-2-yl)hexyl)oxy)isophthalohydrazide,
   j) (5-((4-(Furan-2-yl)butyl)oxy)-1,3-phenylene)dimethanol, or
   k) (5-((6-(Furan-2-yl)hexyl)oxy)-1,3-phenylene)dimethanol.

3. A process for the preparation of novel difunctional monomer compound of formula (I) as claimed in claim 1, wherein said process comprising the steps of :
   a) reacting 5-hydroxyisophthalic acid with methanol in presence of sulfuric acid followed by heating the reaction at temperature in the range of 55 to 65 ° C. for the period of 8 to 10 h to afford dimethyl 5-hydroxyisopthalate;
   b) etherification of the phenolic hydroxyl group of compound of step (a) using α-bromo-ω-furyl alkane at a temperature in the range of 45 to 55 ° C. for the period of 6 to 9 h to afford intermediate diester;
   c) stirring the reaction mixture of intermediate diester of step (b) in ethanol and hydrazine hydrate at temperature in the range of 65 to 75 ° C. for the period in the range of 9 to 12 h to afford 5-((furan-2-yl)alkyl)oxy)isophthalohydrazide;
   d) subjecting intermediate diester of step (b) for reduction in presence of suitable reducing agent to afford (5-((furan-2-yl)alkyl)oxy-1,3-phenylene)dimethanol;
   e) hydrolyzing the intermediate diester of step (b) at a temperature in the range of 55 to 65 ° C. for the period of 10 to 12 h to afford aromatic diacid monomers containing pendant furyl group connected via alkoxy chain;
   f) reacting aromatic diacid monomers of step (e) with triethylamine and ethylchloroformate followed by reaction with sodium azide to afford 5-((furan-2-yl)alkyl) oxy)isophthaloyl azide;
   g) heating the reaction mixture of diacyl azide of step (f) in toluene in presence of nitrogen atmosphere at temperature in the range of 70 to 90 ° C. for the period in the range of 3 to 9 h to afford 2-(3,5-diisocyanatophenoxy)alkyl)furan.

4. The process as claimed in claim 3, wherein alkaline hydrolysis is carried out by using suitable hydrolysis agent selected from sodium hydroxide and potassium hydroxide.

5. The process as claimed in claim 3, wherein said reducing agent in step (d) is selected from lithium aluminium hydride or combination of sodium borohydride and zinc chloride.

6. The compound as claimed in claim 1, wherein said monomer compound of formula (I) is useful for the preparation of self-healable /cross linkable polymers selected from polyurethanes, polyureas and high performance polymers such as aromatic polyimides, aromatic polyamides, aromatic polyesters, aromatic polyhydrazides.

7. A process for the preparation of polyurethane from the compound of formula (I), wherein the said process for the preparation of polyurethane comprises heating the reaction mixture comprising diacyl azide monomer of formula (I) in toluene for 3 h at 70 to 90 ° C. followed by the addition of catalyst and diol dissolved in toluene and further heating the mixture for the period in the range of 7 to 9 h at the same temperature.

8. The process as claimed in claim 7, wherein said catalyst is selected from dibutyltin dilaurate, zirconium acetyl acetonate, 1,5,7-tri-azabicyclo[4.4.0]dec-5-ene, 1,8-biazabicyclo [5.4.0]undec-7-ene, 1,4-diazabicyclo[2.2.2]octane and triethylamine.

9. The process as claimed in claim 7, wherein said diacyl azide monomer compound of formula (I) is 5-((4-(furan-2-yl)butyl)oxy)isophthaloyl azide.

10. The process as claimed in claim 7, wherein diol is selected from α,ω-alkanediol, poly(ethylene glycol) and poly(tetramethylene glycol).

* * * * *